United States Patent [19]

Sherlock

[11] Patent Number: 4,579,857

[45] Date of Patent: Apr. 1, 1986

[54] ANTI-INFLAMMATORY 1-MERCAPTOALKYL-SUBSTITUTED-2-IMIDAZOLIDINONE DERIVATIVES, COMPOSITION, AND METHOD OF USE THEREFOR

[75] Inventor: Margaret H. Sherlock, Bloomfield, N.J.

[73] Assignee: Schering Corporation, Kenilworth, N.J.

[21] Appl. No.: 466,262

[22] Filed: Feb. 14, 1983

[51] Int. Cl.[4] ............... A61K 31/415; A61K 31/455; C07D 401/12; C07D 207/27
[52] U.S. Cl. .................... 514/341; 514/392; 546/278; 548/318; 548/320
[58] Field of Search ............. 548/320, 318; 546/278; 424/273 N; 514/341, 392

[56] References Cited

U.S. PATENT DOCUMENTS 4,376,769  6/1981  Sherlock .................... 544/48

OTHER PUBLICATIONS

Kumar et al., *Journal of Immuno-Pharmacology*, 2(1), 73-83 (1980).
Goodman et al., *The Pharmaceutical Basis of Therapeutics* (Textbook), 6th ed. Macm. Pub. Co., N.Y. 1980, p. 28.
*Chemische Berichte Jahrg.* 97, 1964, pp. 3407-3417, Hellmut Bredereck et al.
*Heterocycles*, vol. 3, No. 1, 1975, pp. 19-23, Toshiyasu Endo et al.
*Organic Chemistry of Sulfur*, 1977, Plenum Press, New York and London, edited by S. Oae., pp. 120-122 and 303-321.
*Liebigs Ann. Chem.*, 1980, pp. 542-556, Siegfried Linke et al.

*Primary Examiner*—Henry R. Jiles
*Assistant Examiner*—J. G. Mullins
*Attorney, Agent, or Firm*—James R. Nelson; Stephen I. Miller

[57] ABSTRACT

1-Mercaptoalkyl-substituted-2-imidazolidinones having anti-inflammatory activity are disclosed. Methods for their preparation and use are described.

5 Claims, No Drawings

ANTI-INFLAMMATORY 1-MERCAPTOALKYL-SUBSTITUTED-2-IMIDAZOLIDINONE DERIVATIVES, COMPOSITION, AND METHOD OF USE THEREFOR

The present invention relates to 1-mercaptoalkyl-5-substituted-2-imidazolidinones. These compounds are useful as anti-inflammatory and/or immunomodulating agents in treating inflammatory conditions such as rheumatoid arthritis, osteoarthritis, tendonitis, SLE and bursitis in mammals.

The compound 1-(2-mercaptoethyl)-4-phenyl-2-imidazolidinone is described in J. Immunopharmacology 2(1), 73, (1980).

The present invention relates to a compound having the structural formula:

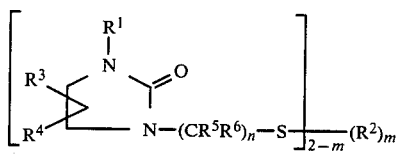

wherein:
m is 0 or 1;
n is 2, 3, 4 or 5;
$R^1$ is hydrogen, alkyl, aralkyl, acyl or aroyl;
$R^2$ is hydrogen, alkyl, acyl, pyridylcarbonyl, aralkyl, aroyl, $-SC(CH_3)_2CH(NH_2)CO_2H$, $H_2NCH(CO_2H)(CH_2)_2CONHCH(CH_2S-)-CONHCH_2CO_2H$, $-SCH_2CH(NH_2)CO_2H$ or carboxyalkyl;
$R^3$ and $R^4$ are independently hydrogen, alkyl, aryl, aralkyl, pyridyl, substituted pyridyl, indolyl, substituted indolyl, pyrimidyl or substituted pyrimidyl; and
$R^5$ and $R^6$ are independently hydrogen or $C_1$ to $C_4$ alkyl;
provided that 1-(2-mercaptoethyl)-4-phenyl-2-imidazolidinone is excluded.

Preferred compounds are those wherein n is 3.

More preferred compounds are those having the names: 1-(3-mercaptopropyl)-5-phenyl-2-imidazolidinone; 1-(3-benzoylthiopropyl)-5-phenyl-2-imidazolidinone; and 1-(3-mercapto-3-methyl)butyl-5-phenylimidazolidin-2-one.

As noted herein, the following terms, unless specified otherwise, are understood to be defined as follows:

The alkyl, alkylene, acyl and alkoxy groups referred to above may have 1 to 8 carbon atoms (2 to 8 for alkylene). Such alkyl groups or alkyl portions of other groups may be a straight chain, a branched chain, a cyclic structure (i.e., cycloalkyl) or combinations thereof. The term alkyl includes methyl, ethyl, propyl, butyl, pentyl, hexyl, heptyl and octyl and isomers thereof such as isopropyl, t-butyl, neopentyl dimethylbutyl and the like. Acyl includes formyl, acetyl, pivaloyl and the like. Cycloalkyl groups may have 3 to 8 carbon atoms in the ring and include cyclopropyl, cyclobutyl, cyclopentyl, cyclohexyl, cycloheptyl and cyclooctyl.

Aryl (or ara as used when the aryl group is part of a larger radical, e.g. aralkyl) is phenyl, substituted phenyl, naphthyl, substituted naphthyl, or substituted or unsubstituted heterocyclic aryl wherein the heterocyclic ring may be derived from pyridine, pryimidine, indole, furan, thiophene or pyrrole. The possible substitutents are set forth below.

The substituted phenyl, naphthyl, and heterocyclic aryl groups referred to above may be substituted with one to three radicals that are independently selected from halogen (i.e., fluoro, chloro, bromo, iodo), $C_1$ to $C_6$ alkyl, $C_1$ to $C_6$ alkoxy, $C_1$ to $C_6$ alkylthio, $C_1$ to $C_6$ alkylsulfinyl, trifluoromethylthio and trifluoromethyl.

The compounds of the invention contain a —$(CR^5R^6)_n$— substituent wherein the $R^5$ and $R^6$ groups may vary independently. Thus, for example, when n equals 3 the following patterns of substitution (wherein $CH_3$ is used to represent any substituent) are contemplated: —$(CH_2)_3$—, —$CH_2CH(CH_3)CH_2$—, —$(CH_2)_2C(CH_3)_2$—, —$CH_2C(CH_3)_2CH_2$—, —$CH(CH_3)CH_2CH_2$—, —$(C(CH_3)H)_3$— and the like.

The compounds of the present invention may be prepared by the base-catalyzed hydrolysis of the appropriately substituted compound of the structural formula II as follows:

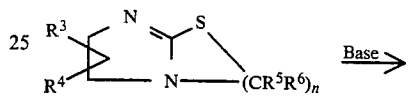

II

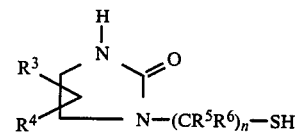

III

Derivatization of the sulfhydryl group and/or of the ring nitrogen atom can be carried out by alkylation, esterification, etc. as is well known in the art. For example, a 1-substituted derivative is prepared as follows:

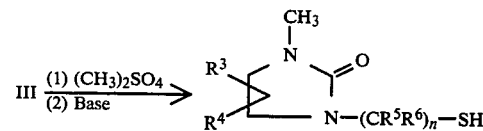

The compounds having structural formula II are described and prepared in U.S. patent application Ser. No. 275,166, filed June 19, 1981, now U.S. Pat. No. 4,376,769.

Certain of the compounds having structural formula I may contain one or more asymmetric centers. The invention contemplates all such possible isomers both in pure form and in admixture including racemic mixtures.

The compounds of the invention having a thiol group, i.e. compounds having structural formula I wherein m is 1 and $R^2$ is hydrogen, form metal salts with pharmaceutically acceptable metals by art recognized methods. Thus, for example, the sodium, potassium, zinc, copper and gold salts may be prepared. The thiol compounds also form (trialkylphosphine)gold complexes. For example, a thiol compound may be treated with chloro(triethylphosphine)gold by well known methods (e.g. see U.S. Pat. No. 3,947,565) to produce the corresponding (triethylphosphine)gold complex.

For purposes of the invention, the above described metal salts and complexes are considered to be equivalent to the compounds having structural ormula I.

The anti-inflammatory potential of the compounds of the present invention may be determined by the Reversed Passive Arthus Response technique as set forth below using male Lewis inbred albino rate (Charles River) weighing 180-200 grams. The potency of the compounds is determined using indomethacin as the standard. On the basis of the test results, a dosage range of 1 mpk to about 200 mpk in divided doses taken at about 4 hour intervals is recommended.

Reversed Passive Arthus Response (RPAR) Animals, Materials and Methods

Male Lewis inbred albino rats weighing 180-200 grams obtained from Charles River Breeding Laboratories are used in these experiments. The rats are housed 3 animals/cage and food and water are allowed ad libitum. The animals are numbered 1-3 in each cage and color marked for identification purposes.

Drug and Reagent Preparation

All reagents and drugs are prepared just prior to the study. Crystallized and lyophylized bovine serum albumin (BSA), obtained from Sigma Chemical Company, is solubilized without shaking in cold sterile pyrogen free saline (10 mg/ml). Lyophylized anti-bovine serum albumin (IGG fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after the last dose the animals are lightly anesthetized with ether and "sensitized" by injection into the penile vein with 0.2 ml of PFS containing 1.0 mg of BSA. One hour later, the animals are "challenged" in the right rear paw with subplantar injections of 0.2 ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are also recorded with a plethysmograph during the development of the inflammation at 2 and 4 hours post-challenge.

Results

Results are expressed by the change in paw volume (Δ paw volume) from the control reading for each animal to that recorded 2 and 4 hours post-challenge. All drug treated groups are compared to the MC control for significant differences with an analysis of variance. Differences from control in drug-treated groups are expressed as percent change from control.

The dosage to be administered depends upon the particular compound used, the age and general health of the patient and the severity of the inflammatory condition. Thus, the dose ultimately decided upon may be left to the judgement of a trained health-care practitioner.

The compounds of this invention may be processed and dispensed by well known methods and in unit dosage form. For example, tablets, capsules, and elixirs, for oral administration; solutions and suspensions for parenteral administration; creams, lotions and sprays for topical administration; as well as suppositories for rectal administration are contemplated. In whatever form the compounds are dispensed, they may be admixed with pharmaceutically acceptable excipients, binders, dispersing agents, lubricants, flavorants, preservatives and carriers generally used in the art.

Exemplary of the pharmaceutical carriers, excipients, preservatives and binders are gelatin, lactose, starch, magnesium stearate, sugar, talc, vegetable oils, gums, saccharin, polyalkylene glycols, etc. The pharmaceutical dosage forms are prepared by the methods conventionally used in the art. Further, the dosage units may also contain a compatible anti-depressant and/or analgesics to treat the depression and pain usually associated with chronic inflammatory conditions.

The following examples illustrate the preparation of the compounds of the invention.

EXAMPLE I 1-(3-Mercaptopropyl)-5-phenyl-2-imidazolidinone

A mixture of 55.0 g of 3-phenyl-2,3,6,7-tetrahydro-5H-imidazo[2,1-b][1,3]thiazine and 540 ml of 0.5N sodium hydroxide solution is stirred and refluxed under nitrogen for thirty hours. The solution is cooled, neutralized to pH 8 with carbon dioxide and extracted with methylene chloride. The organic extracts are dried over magnesium sulfate, filtered and concentrated in vacuo to yield a colorless solid. Recrystallization from isopropyl acetate yields the product of this example, 53.8 g, m.p. 97°-99° C.

EXAMPLE II 1-(3-Benzoylthiopropyl)-5-phenyl-2-imidazolidinone

To a solution of 1-(3-mercaptopropyl)-5-phenyl-2-imidazolidinone-2, 20 g, in 300 ml of methylene chloride there is added 8.6 g of triethylamine. To the cooled, stirred solution there is added, dropwise, 12 g of benzoyl chloride and the solution allowed to reach room temperature overnight. To the reaction mixture is added 250 ml water, the organic layer separated and washed with water, dried over magnesium sulfate and concentrated in vacuo to a solid residue. The product is recrystallized from ethyl acetate-isopropyl ether yielding a colorless solid, 22.9 g, m.p. 112°-115° C.

EXAMPLE III 1-(3-Mercapto-3-methyl)butyl-5-phenyl-2-imidazolidinone

A solution of 3 g of 7,7-dimethyl-3-phenyl-2,3,6,7-tetrahydro-5H-imidazo[2,1-b][1,3]thiazine in 26 ml of 0.5N sodium hydroxide solution and 20 ml of pyridine is refluxed for three days. The solvent is removed in vacuo, the reaction mixture neutralized with carbon dioxide and extracted with methylene chloride. The organic layer is separated, dried over magnesium sulfate and concentrated to a solid. Recrystallization from isopropyl ether yields the product as a colorless solid, m.p. 135°–138° C.

EXAMPLE IV

Methyl-[3-(2-oxo-4-phenyl-3-imidazolidinyl)propyldithio]formate

To a solution of 6.7 g of 1-(3-mercaptopropyl-5-phenyl-2-imidazolidinone in 70 ml of methanol, cooled to 0°, there is added dropwise 3.9 g of methoxy carbonylsulfenyl chloride over a fifteen minute period. The solution is allowed to stir at 0° for 1 hour and at room temperature for four hours. The reaction is concentrated in vacuo and the residual oil eluted on a silica gel column with ethyl acetate. The product is purified further by recrystallization from isopropyl ether, m.p. 98°–100° C.

EXAMPLE V

S-[3-(2-oxo-4-phenyl-3-imidazolidinyl)propylthio]cysteine

A solution of 3.3 g of methyl-[3-(2-oxo-4-phenyl-3-imidazolidinyl)propylthio]formate and 1.8 g of L-cysteine hydrochloride hydrate in 80 ml of methanol is refluxed under nitrogen for three hours. The solvent is removed in vacuo and the residue triturated with ether yielding a hygroscopic solid. The product is further purified by conversion to its 4-methyl benzene sulfonic acid salt, m.p. 172°–178° C.

EXAMPLE VI 1-(4-Mercaptobutyl)-5-(4-fluorophenyl)-2-imidazolidinone

A mixture of 2.9 g of 7-(4-fluorophenyl)-2,3,4,5,7,8-hexahydroimidazo[2,1-b][1,3]thiazepine hydrochloride and 25 ml of 1N sodium hydroxide solution is stirred and heated at reflux for forty five hours. The reaction is processed in the usual manner yielding the product of this example, m.p. 102°–104° after recrystallization from isopropyl acetate-isopropyl ether.

I claim:

1. A compound having the structural formula:

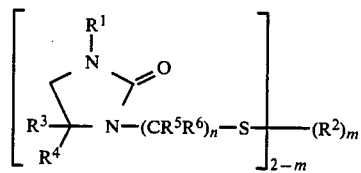

wherein:
   m is 0 or 1;
   n is 3, 4 or 5;
   $R^1$ is hydrogen, lower alkyl, lower cycloalkyl, phenyl-lower alkyl, substituted phenyl-lower alkyl, naphthyl-lower alkyl, substituted naphthyl-lower alkyl, lower alkanoyl, benzoyl, substituted benzoyl, naphthoyl, or substituted naphthoyl;
   $R^2$ is hydrogen, lower alkyl, lower cycloalkyl, lower alkanoyl, pyridylcarbonyl, phenyl-lower alkyl, substituted phenyl-lower alkyl, naphthyl-lower alkyl, substituted naphthyl-lower alkyl, benzoyl, substituted benzoyl, naphthoyl, substituted naphthoyl, —SC(CH$_3$)$_2$CH(NH$_2$)CO$_2$H, H$_2$NCH(CO$_2$H)(CH$_2$)$_2$CONHCH(CH$_2$S—)-CONHCH$_2$CO$_2$H, —SCH$_2$CH(NH$_2$)CO$_2$H or carboxyalkyl;
   $R^3$ and $R^4$ are independently hydrogen, lower alkyl, lower cycloalkyl phenyl, substituted phenyl, naphthyl, substituted naphthyl, phenyl-lower alkyl, substituted phenyl-lower alkyl, or naphthyl-lower alkyl, substituted naphthyl-lower alkyl; and
   $R^5$ and $R^6$ are independently hydrogen or $C_1$ to $C_4$ alkyl;
   wherein the substituents on the substituted phenyl or substituted naphthyl moeities may be one to three radicals that are independently selected from halo, $C_1$ to $C_6$ alkyl, $C_1$ to $C_6$ alkoxy, $C_1$ to $C_6$ alkylthio, $C_1$ to $C_6$ alkylsulfinyl, trifluoromethylthio and trifluoromethyl.

2. The compounds defined in claim 1 wherein n is 3.

3. The compounds defined in claim 1 having the names: 1-(3-mercaptopropyl)-5-phenyl-2-imidazolidinone; 1-(3-benzoylthiopropyl)-5-phenyl-2-imidazolidinone; and 1-(3-mercapto-3-methyl)butyl-5-phenylimidazolidin-2-one.

4. An anti-inflammatory pharmaceutical composition which comprises an effective amount of a compound defined in claim 1 in combination with a pharmaceutically acceptable carrier.

5. A method for treating inflammation in a mammal which comprises administering the composition defined in claim 4 to said mammal.

* * * * *